(12) United States Patent
Yorimoto et al.

(10) Patent No.: US 10,537,398 B2
(45) Date of Patent: Jan. 21, 2020

(54) MEDICAL MANIPULATOR SYSTEM

(71) Applicant: OLYMPUS CORPORATION, Tokyo (JP)

(72) Inventors: Ryuichi Yorimoto, Tokyo (JP); Takahiro Komuro, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 134 days.

(21) Appl. No.: 15/697,684

(22) Filed: Sep. 7, 2017

(65) Prior Publication Data

US 2017/0360519 A1 Dec. 21, 2017

Related U.S. Application Data

(63) Continuation of application No. PCT/JP2016/063555, filed on May 2, 2016.

(30) Foreign Application Priority Data

May 29, 2015 (JP) .................................. 2015-109758

(51) Int. Cl.
*A61B 34/37* (2016.01)
*B25J 13/08* (2006.01)
(Continued)

(52) U.S. Cl.
CPC .......... *A61B 34/37* (2016.02); *A61B 1/00149* (2013.01); *A61B 34/74* (2016.02);
(Continued)

(58) Field of Classification Search
CPC . A61B 34/37; A61B 1/00039; A61B 1/00057; B25J 3/00; B25J 3/04; B25J 3/1692; B25J 13/02; B25J 13/088
See application file for complete search history.

(56) References Cited

U.S. PATENT DOCUMENTS

| | | | |
|---|---|---|---|
| 2009/0326318 A1 | 12/2009 | Tognaccini et al. | |
| 2013/0211592 A1* | 8/2013 | Kim .......................... | B25J 3/00 700/258 |
| 2018/0092700 A1* | 4/2018 | Itkowitz ................. | A61B 34/25 |

FOREIGN PATENT DOCUMENTS

| | | | |
|---|---|---|---|
| EP | 2324789 A1 | 5/2011 | |
| EP | 2881061 A1 | 6/2015 | |
| (Continued) | | | |

OTHER PUBLICATIONS

International Search Report dated Aug. 2, 2016 issued in PCT/JP2016/063555.

(Continued)

*Primary Examiner* — Spencer D Patton
(74) *Attorney, Agent, or Firm* — Scully, Scott, Murphy & Presser, P.C.

(57) ABSTRACT

A medical manipulator system includes a manipulator having a first joint; a first detecting means detecting an orientation of the first joint; an operation unit having a second joint associated with the first joint for operating the first joint; a second detecting means detecting an orientation of the second joint; a control unit outputting a signal for operating the first joint, the signal being based on the orientation of the second joint detected by the second detecting means; and a display unit displaying information output by the control unit, wherein a display of the information by the display unit includes a first display indicating a predetermined range of an orientation determined by using the orientation of the first joint that is detected by the first detecting means as a reference and a second display indicating the orientation of the second joint that is detected by the second detecting means.

4 Claims, 10 Drawing Sheets

(51) Int. Cl.
  *B25J 13/02*  (2006.01)
  *B25J 3/04*   (2006.01)
  *B25J 3/00*   (2006.01)
  *A61B 34/00*  (2016.01)
  *A61B 1/00*   (2006.01)
  *A61B 17/00*  (2006.01)

(52) U.S. Cl.
  CPC . *B25J 3/00* (2013.01); *B25J 3/04* (2013.01); *B25J 13/02* (2013.01); *B25J 13/088* (2013.01); *A61B 2017/00367* (2013.01)

(56) References Cited

FOREIGN PATENT DOCUMENTS

| | | |
|---|---|---|
| JP | H06-297368 A | 10/1994 |
| JP | 2001-104333 A | 4/2001 |
| JP | 2003-265500 A | 9/2003 |
| JP | 2005-335000 A | 12/2005 |
| JP | 2013-034851 A | 2/2013 |
| JP | 2014-028007 A | 2/2014 |
| JP | 2014-097431 A | 5/2014 |
| JP | 2016-514492 A | 5/2016 |
| WO | 2010/055745 A1 | 5/2010 |
| WO | 2013/018936 A1 | 2/2013 |
| WO | WO 2014/146095 A1 | 9/2014 |
| WO | WO 2014/199415 A1 | 12/2014 |

OTHER PUBLICATIONS

Notice of Allowance dated Apr. 25, 2017 issued in JP 2017-508711.
Extended Supplementary European Search Report dated Jan. 28, 2019 in European Patent Application No. 16 80 2976.7.

* cited by examiner

MEDICAL MANIPULATOR SYSTEM

This application is a continuation application based on PCT International Application No. PCT/JP2016/063555, filed on May 2, 2016, whose priority is claimed on Japanese Patent Application No. 2015-109758, filed on May 29, 2015. The contents of both of the PCT International Application and the Japanese Patent Application are incorporated herein by reference.

BACKGROUND OF THE INVENTION

Field of the Invention

The present invention relates to a medical manipulator system.

Description of Related Art

Conventionally, a manipulator system used for medical use is known.

For example, in PCT International Publication No. WO2010/055745, a medical system including an insertion slave device being used together with a treatment slave device and an insertion master which is similar in type to the treatment slave device is disclosed.

For example, in Japanese Unexamined Patent Application, First Publication No. 2013-034851, a medical manipulator system including an opening/closing portion capable of an opening and closing operation for treatment inside the body and a master grasp capable of an opening and closing manipulation for performing a manipulation input with respect to the opening/closing portion is disclosed.

For example, in Japanese Unexamined Patent Application, First Publication No. H06-297368, as a control device controlling an operation of a manipulator having at least one joint, a device which corrects an input value to remove an external disturbance applied to a control system of the joint based on the input value provided to the joint and an output value generated by the input value is disclosed.

SUMMARY OF THE INVENTION

According to a first aspect of the present invention, a medical manipulator system includes a manipulator having a first joint, a first detecting means detecting an orientation of the first joint, an operation unit having a second joint associated with the first joint for operating the first joint, a second detecting means detecting an orientation of the second joint, a control unit outputting a signal for operating the first joint based on the orientation of the second joint detected by the second detecting means, and a display unit displaying information output by the control unit, wherein a display of the information by the display unit includes a first display and a second display, the first display indicating a predetermined range of an orientation determined by using the orientation of the first joint that is detected by the first detecting means as a reference, and the second display indicating the orientation of the second joint that is detected by the second detecting means.

According to a second aspect of the present invention, in the medical manipulator system according to the first aspect, the control unit may output a signal for operating the first joint such that an angle of the first joint coincides with an angle of the second joint, when the orientation of the second joint is within the range indicated by the first display.

According a third aspect of the present invention, in the medical manipulator system according to the first aspect, the control unit may output the information indicating an angle of the second joint with respect to an angle of the first joint to the display unit.

According a fourth aspect of the present invention, in the medical manipulator system according to the third aspect, the control unit may calculate an operation procedure of the second joint until the angle of the second joint coincides with the angle of the first joint based on the angle of the first joint and the angle of the second joint and output the information indicating the calculated operation procedure to the display unit.

DETAILED DESCRIPTION OF THE INVENTION

First Embodiment

Figure 1:
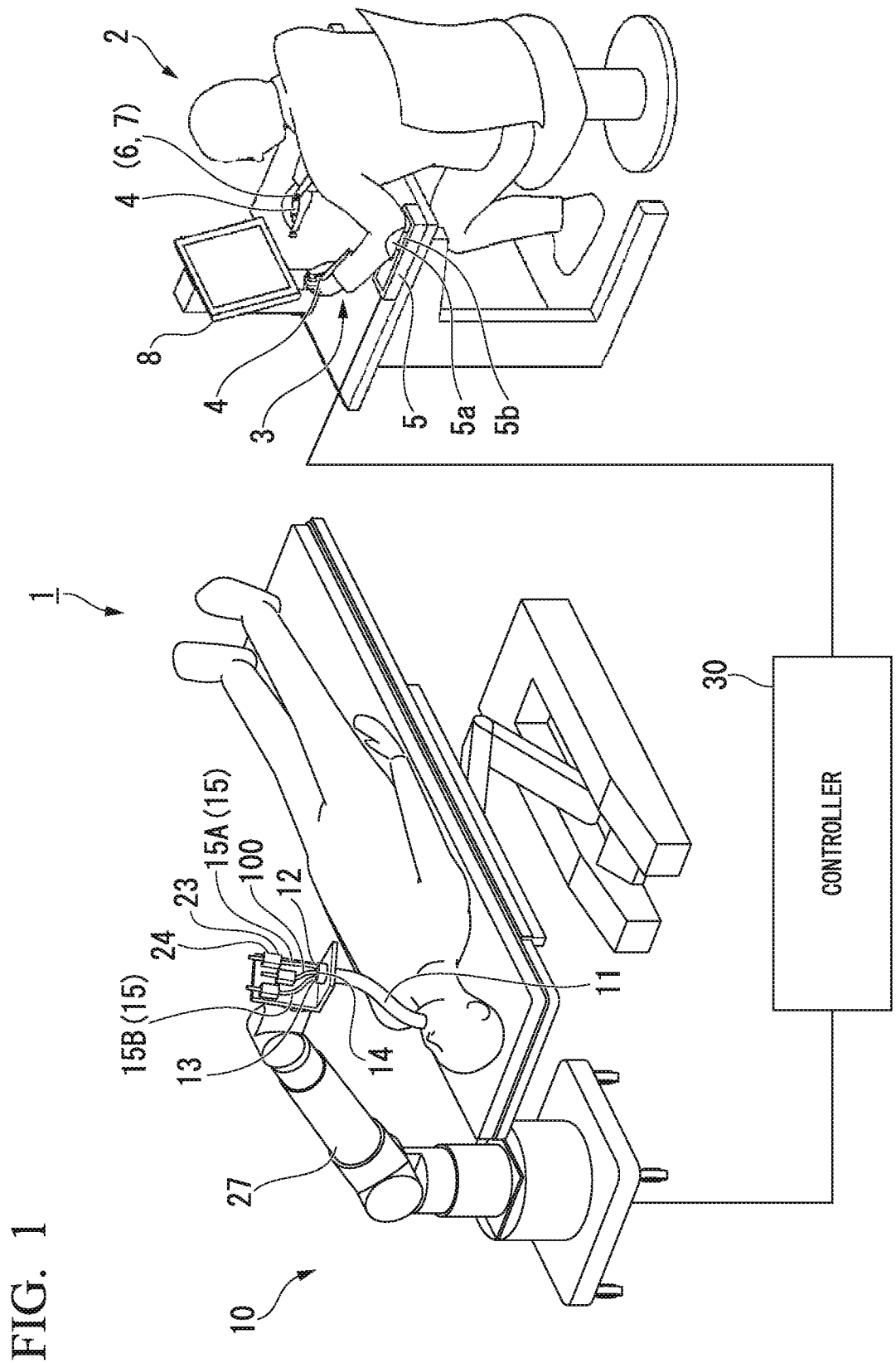
FIG. 1 is a general view showing a medical manipulator system of a first embodiment of the present invention.
Figure 2:
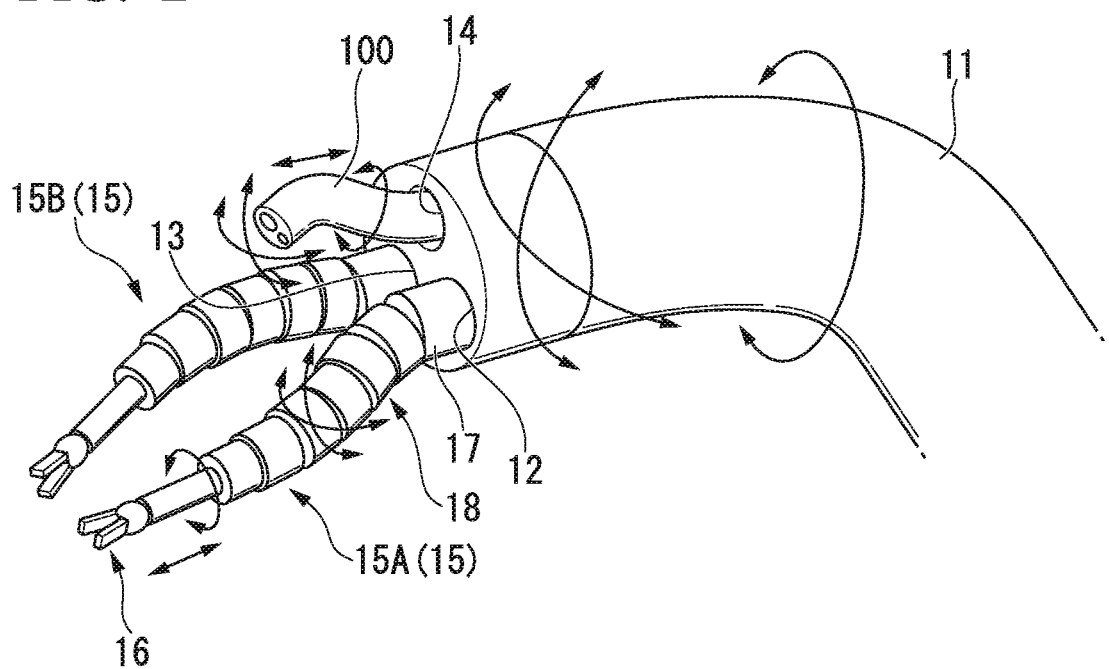
FIG. 2 is a perspective view showing a part of the medical manipulator system.
Figure 3:
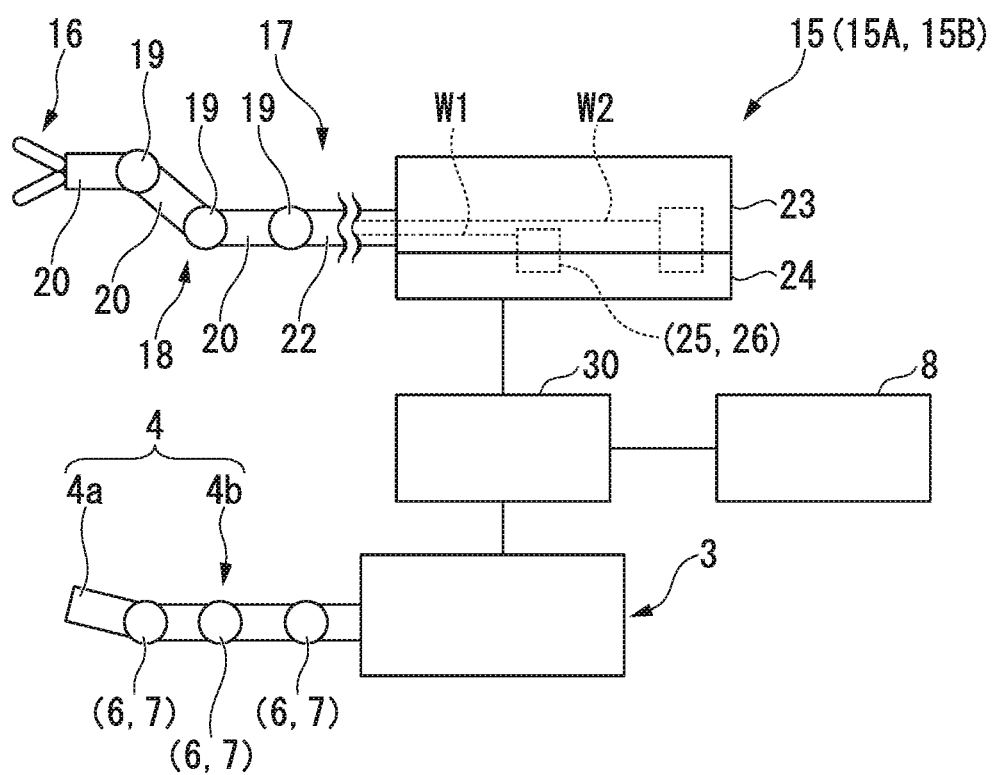
FIG. 3 is a schematic view of the medical manipulator system.
Figure 4:
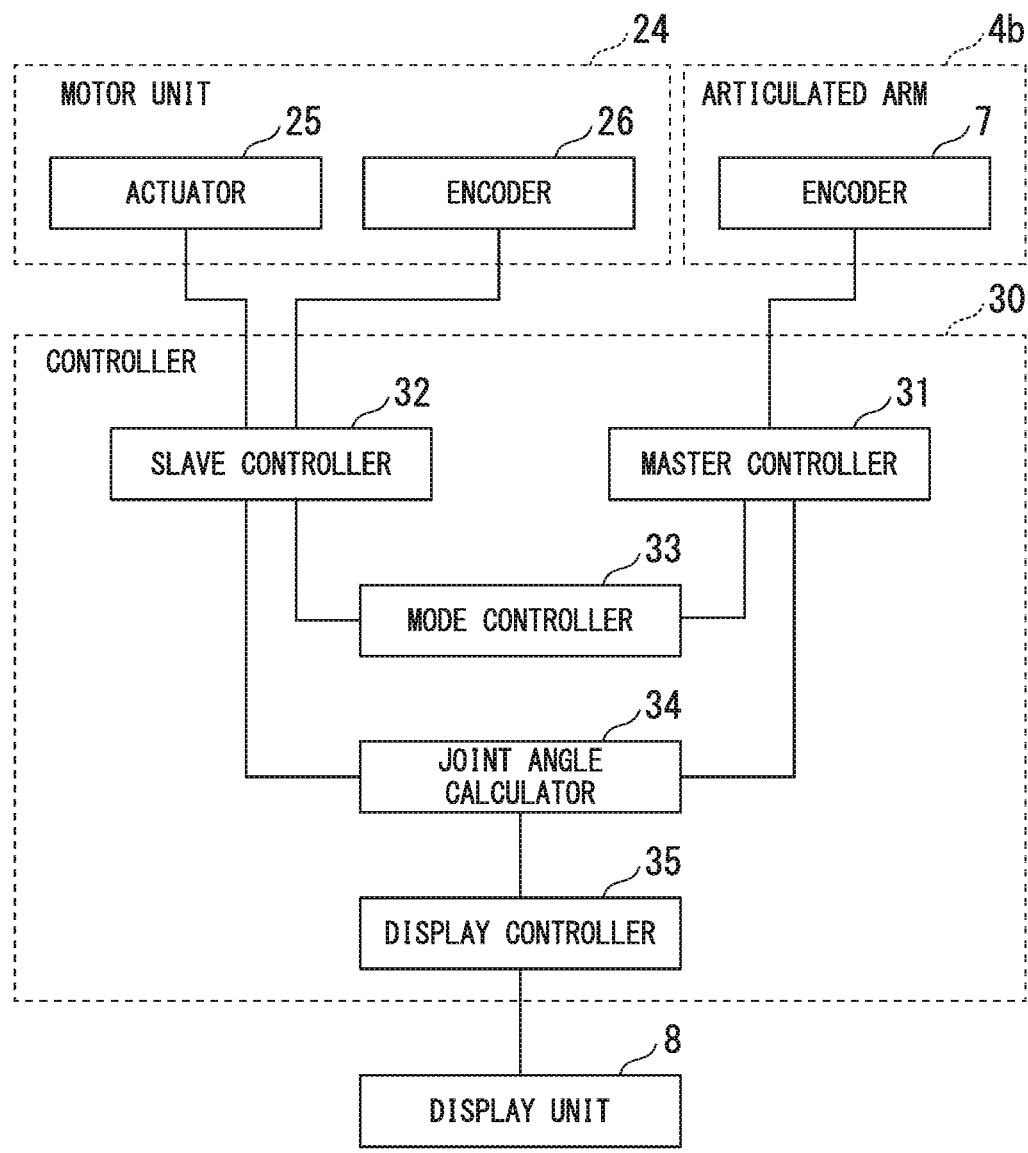
FIG. 4 is a block diagram of the medical manipulator system.

A first embodiment of the present invention will be described. FIG. 1 is a general view showing a medical manipulator system of the present embodiment. FIG. 2 is a perspective view showing a part of a medical manipulator system. FIG. 3 is a schematic view of a medical manipulator system. FIG. 4 is a block diagram of a medical manipulator system.

A medical manipulator system 1 of the present embodiment shown in FIG. 1 includes a master manipulator 2, a slave manipulator 10, and a controller 30 (a control unit).

The master manipulator 2 has an operation input device 3 and a display unit 8.

The operation input device 3 is provided for operating medical instruments such as a treatment instrument 15, an endoscope 100, or the like to be described below provided in the slave manipulator 10 from the outside of the body. As shown in FIGS. 1 and 3, the operation input device 3 includes an operation unit 4 grasped by an operator for operating the operation input device 3 and a linear motion mechanism 5 on which an elbow of the operator can be placed.

As shown in FIG. 3, the operation unit 4 includes an articulated arm 4*b* having a grasp portion 4*a* grasped by the operator and a plurality of joints 6 (second joints) and encoders 7 (second detecting means). An operation of the operator grasping the operation unit 4 of the operation input device 3 to move the articulated arm 4*b* is converted by each of the encoders 7 into information necessary for operating the treatment instrument 15, the endoscope 100, or the like (see FIGS. 1 and 2).

As shown in FIG. 3, the articulated arm 4*b* of the present embodiment corresponds to the configuration of a joint portion 18 provided in the treatment instrument 15. The articulated arm 4*b* has the same degree of freedom as the joint portion 18 of the treatment instrument 15 or more to be able to have a similar shape to a shape of the joint portion 18 of the treatment instrument 15.

As shown in FIG. 1, the linear motion mechanism 5 includes an armrest 5*a* and a slider 5*b* fixed to the operation unit 4. The linear motion mechanism 5 is configured to be capable of moving a position of the operation unit 4 while maintaining an orientation of grasping the operation unit 4 by moving the slider 5*b* in a horizontal direction by an arm placed on the armrest 5*a*. By moving the operation unit 4 using the linear motion mechanism 5, an amount of protrusion of an elongated portion 17 from a medical overtube 11 on a slave side can be operated and thus the treatment instrument 15 can be moved.

The display unit 8 is provided for displaying images captured by the endoscope 100 to be described below, information necessary for operating the medical manipulator system 1 of the present embodiment, or the like. The display unit 8 is connected to the controller 30. The display unit 8 displays images based on video signals output from the controller 30. The configuration of the display unit 8 is not particularly limited.

As shown in FIG. 1, the slave manipulator 10 includes the medical overtube 11, the treatment instrument 15, a motor unit 24, and a slave arm 27.

As shown in FIG. 2, the medical overtube 11 includes a first lumen 12 and a second lumen 13 to which the treatment instrument 15 is attached, and a third lumen 14 to which the endoscope 100 is attached. The medical overtube 11 only has to be a tubular shape which can be inserted into a digestive tract or the like through a natural opening such as a mouth of a patient. The medical overtube 11 may be able to perform a bending operation as needed according to an operation outside the body. Further, the medical overtube 11 is not limited to the configuration described above, and may also have a configuration in which the treatment instrument 15 is fixed to the medical overtube 11 in a state in which the treatment instrument 15 protrudes from a distal end of the medical overtube 11.

The treatment instrument 15 is a manipulator which can be attached to the first lumen 12 or the second lumen 13 of the medical overtube 11. In the present embodiment, the treatment instrument 15 includes a first treatment instrument 15A which can be inserted into the first lumen 12 to be able to advance from and retreat into the first lumen 12 of the medical overtube 11 and a second treatment instrument 15B which can be inserted into the second lumen 13 to be able to advance from and retreat into the second lumen 13 of the medical overtube 11. Further, the medical manipulator system 1 of the present embodiment is not limited to having two treatment instruments 15 and may have only one treatment instrument 15 or may have three or more treatment instruments 15.

In the present embodiment, the first treatment instrument 15A and the second treatment instrument 15B have configurations for performing treatment such as incision, grasping, or suturing on a treatment target region inside the body. The configurations of the first treatment instrument 15A and the second treatment instrument 15B may be the same as each other or may be different from each other. Hereinafter, the configuration of the first treatment instrument 15A of the two treatment instruments 15 will be described, and the description of the second treatment instrument 15B will be omitted.

As shown in FIG. 3, the first treatment instrument 15A (hereinafter, simply referred to as "treatment instrument 15") includes an end effector 16, the elongated portion 17, and a first proximal end portion 23.

The end effector 16 shown in FIGS. 2 and 3 is provided at a distal end of the treatment instrument 15 to perform a treatment on a treatment target region inside the body.

The configuration of the end effector 16 is not particularly limited as long as it is a treatment portion acting on a treatment target region. The end effector 16, for example, may be one performing a surgical procedure on tissues inside the body such as a grasping forceps, an incision knife, or an electrode, and may also be an optical or ultrasonic observation device for observing the inside of the body. As shown in FIG. 3, the end effector 16, for example, may be a grasping forceps having a pair of jaws which can perform an opening and closing operation according to a pulling operation of a driving wire W2, a knife for incising tissues by applying a high-frequency current, or the like.

The elongated portion 17 shown in FIG. 3 is an elongated flexible member to be inserted into the body to guide the end effector 16 to a treatment target region inside the body. In the present embodiment, the elongated portion 17 has flexibility as a whole and the elongated portion 17 can guide the end effector 16 from a natural opening such as a mouth through a digestive tract or the like to a treatment target region, running along the digestive tract or the like. The elongated portion 17 may have flexibility or may be a rigid member having a substantially linear shape. Hereinafter, an example of a configuration of the elongated portion 17 having flexibility will be shown.

The elongated portion 17 having flexibility includes a joint portion 18 and a flexible tube portion 22.

The joint portion 18 includes a plurality of joint elements 19 (first joints) arranged in a centerline direction of the elongated portion 17 and connected to each other, and a rod-shaped portion 20 connecting each of the joint elements 19. Since the joint portion 18 is bent and deformed at each of the joint elements 19, the joint portion 18 can be bent and deformed as a whole. The plurality of joint elements 19 provided in the joint portion 18 may include those deformable to bend the centerline of the elongated portion 17, those operable to rotate a distal end side with respect to a proximal end side about the centerline of the elongated portion 17, or the like. A joint element 19 on a most distal end side of the joint portion 18 is connected to an angle wire W1 which transmits an amount of force for bending and deforming the joint portion 18 from a side of the first proximal end portion 23.

The flexible tube portion 22 (see FIG. 3) is a tubular member having flexibility to such an extent that it can have a curved shape following a curved shape of the first lumen 12 or the second lumen 13 when the medical overtube 11

(see FIG. 2) is in a curved state. The angle wire W1 for bending and deforming the joint portion 18 and the driving wire W2 for operating the end effector 16 are inserted into the flexible tube portion 22.

The first proximal end portion 23 is attachable to and detachable from the motor unit 24 to be described below. The first proximal end portion 23 receives power for operating the end effector 16 and the joint portion 18 from the motor unit 24 and performs transmission of the power to the angle wire W1 and the driving wire W2.

The motor unit 24 is configured to be as a second proximal end portion attachable to and detachable from the first proximal end portion 23 and the motor unit 24 is attachable to and detachable from a proximal end side of the treatment instrument 15. The motor unit 24 includes an actuator 25 or the like which generates power for operating the end effector 16 and the joint portion 18, and an encoder 26 (a first detecting means) for detecting an angle of each joint element 19. The motor unit 24 operates according to control by a slave controller 32 (see FIG. 4).

As shown in FIG. 1, the slave arm 27 is an articulated robot to which the motor unit 24 (the second proximal end portion) is attached and is operated according to commands given by the slave controller 32 (see FIG. 4) based on an operation by the operator on the master manipulator 2.

As shown in FIG. 4, the controller 30 includes a master controller 31, the slave controller 32, a mode controller 33, a joint angle calculator 34, and a display controller 35.

Based on information output from each encoder 7 (see FIG. 4) according to an operation on the operation input device 3 of the master manipulator 2 shown in FIG. 1, the master controller 31 receives an operation performed by the operator on the operation input device 3, generates predetermined commands for operating the slave controller 32, and outputs them to the slave controller 32. The configuration of the master controller 31 is not particularly limited, and a known operation flow may be appropriately applied.

The slave controller 32 operates the slave arm 27 and the treatment instrument 15 based on the above-described commands generated by the master controller 31 and output to the slave controller 32. That is, the slave controller 32 provides commands to the slave arm 27 and the treatment instrument 15.

The mode controller 33 performs switching between a first mode in which the slave manipulator 10 is operated according to an operation on the master manipulator 2 (see FIG. 1), a second mode in which the treatment instrument 15 and the operation input device 3 are operated so that the treatment instrument 15 provided in the slave manipulator 10 and the operation input device 3 of the master manipulator 2 have a similarity relation, and a third mode in which the slave manipulator 10 does not follow the operation of the master manipulator 2 and a position and orientation of the slave manipulator 10 are held.

The joint angle calculator 34 is provided in the controller 30 to detect an orientation of the joint portion 18 (see FIG. 3) and an orientation of the operation input device 3 (see FIG. 3) in the three modes described above. The joint angle calculator 34 acquires information indicating an angle of each joint 6 from the encoder 7 provided in each of the joints 6 configuring the articulated arm 4b. The joint angle calculator 34 acquires information indicating an angle of each joint 19 from the encoder 26 provided in the motor unit 24. Since the encoder 26 acquires angle information of the actuator 25 of the motor unit, the joint angle calculator 34 calculates the angle of each joint element 19 in consideration of mechanical elements from the actuator to each of the joint elements 19 of the treatment instrument 15.

There may be a configuration in which the encoder 26 is provided in each joint element 19.

The joint angle calculator 34 has information for specifying a predetermined range, for each treatment instrument 15, as a movable range of each joint element 19 provided in the joint portion 18 of the treatment instrument 15. Further, in the movable range of each joint element 19 provided in the joint portion 18 of the treatment instrument 15, as a movement range to such an extent that the end effector 16 or the joint portion 18 do not come into contact with tissues inside the body when the joint portion 18 is operated inside the body, the joint angle calculator 34 defines a certain angle range predetermined with reference to a current position of the joint portion 18 as a shape synchronizable range.

The joint angle calculator 34 outputs information indicating the angle of each joint 6 of the articulated arm 4b and the joint portion 18 of the treatment instrument 15, information indicating the movable range of each joint element 19 provided in the joint portion 18 of the treatment instrument 15, and information indicating the shape synchronizable range described above to the display controller 35.

Based on the information indicating the angle of each joint 6 of the articulated arm 4b and the joint portion 18 of the treatment instrument 15, the information indicating the movable range of each joint element 19 provided in the joint portion 18 of the treatment instrument 15, and the information indicating the shape synchronizable range described above, the display controller 35 generates image information for visually conveying a user the angle of each joint 6 of the articulated arm 4b with respect to the angle of each joint element 19 configuring the joint portion 18 of the treatment instrument 15.

The image information generated by the display controller 35 may be indicated by numerical values based on the information indicating the angle of each joint 6 of the articulated arm 4b and the joint portion 18 of the treatment instrument 15, the information indicating the movable range of each joint element 19 provided in the joint portion 18 of the treatment instrument 15, and the information indicating the shape synchronizable range described above, or may be shown by a figure for allowing a user to intuitively understand an orientation of the operation input device 3 with respect to an orientation of the treatment instrument 15.

Hereinafter, a case in which the display controller 35 shows a figure for allowing a user to intuitively understand the orientation of the operation input device 3 with respect to the orientation of the treatment instrument 15 will be discussed as an exemplary example.

Figure 7:
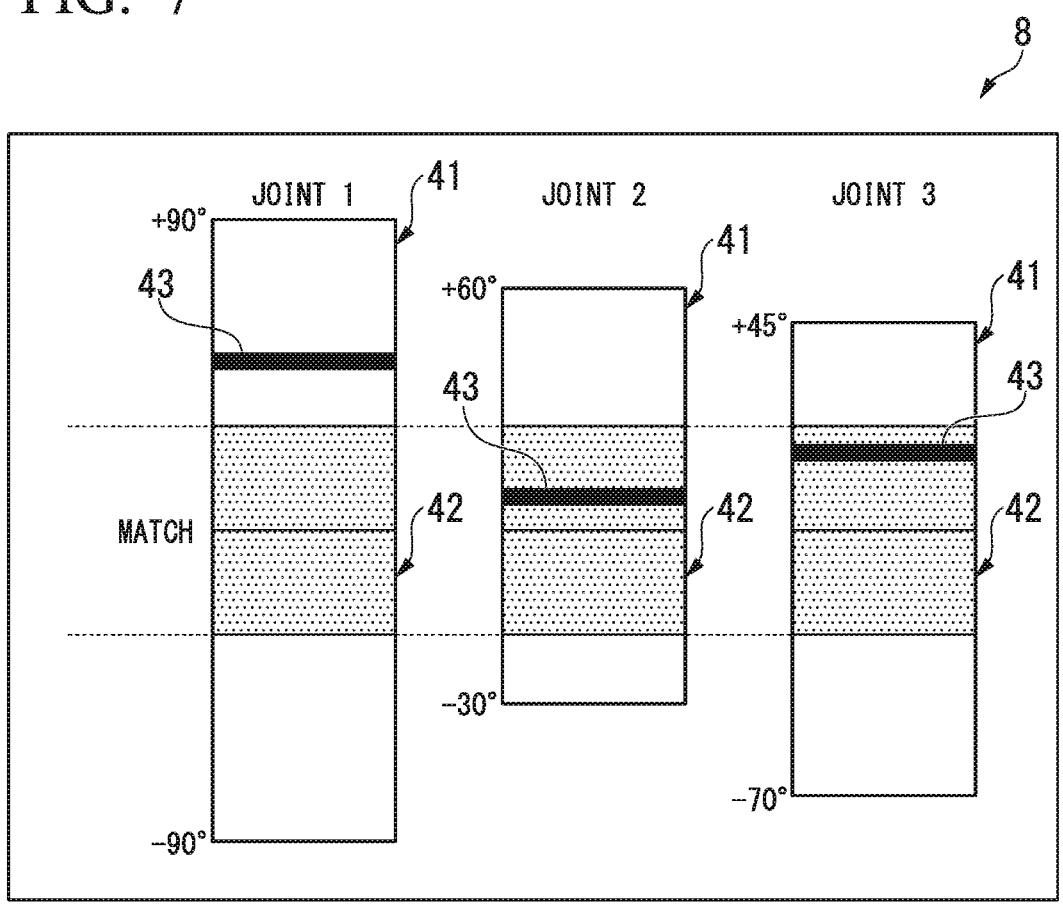
FIG. 7 is a schematic view showing an example of a screen display of a display unit in the medical manipulator system.

The figure displayed on the display unit 8 according to the control of the display controller 35, for example, includes a first frame display 41, a second frame display 42, and a linear display 43 as shown in FIG. 7.

The first frame display 41 shown in FIG. 7 shows the movable range of each joint element 19 in the joint portion 18 of the treatment instrument 15.

The second frame display 42 shown in FIG. 7 shows the above-described shape synchronizable range in the first frame display 41.

The linear display 43 shown in FIG. 7 shows the angle of the joint 6 of the operation input device 3 corresponding to each joint element 19 of the joint portion 18 of the treatment instrument 15 in the first frame display 41.

These displays are displayed on the display unit 8 side by side for each joint element 19 provided in the joint portion 18 of the treatment instrument 15.

A position of the linear display 43 with respect to the first frame display 41 changes according to relative movement of the articulated arm 4b of the operation input device 3 with respect to the joint portion 18 of the treatment instrument 15.

Figure 5:
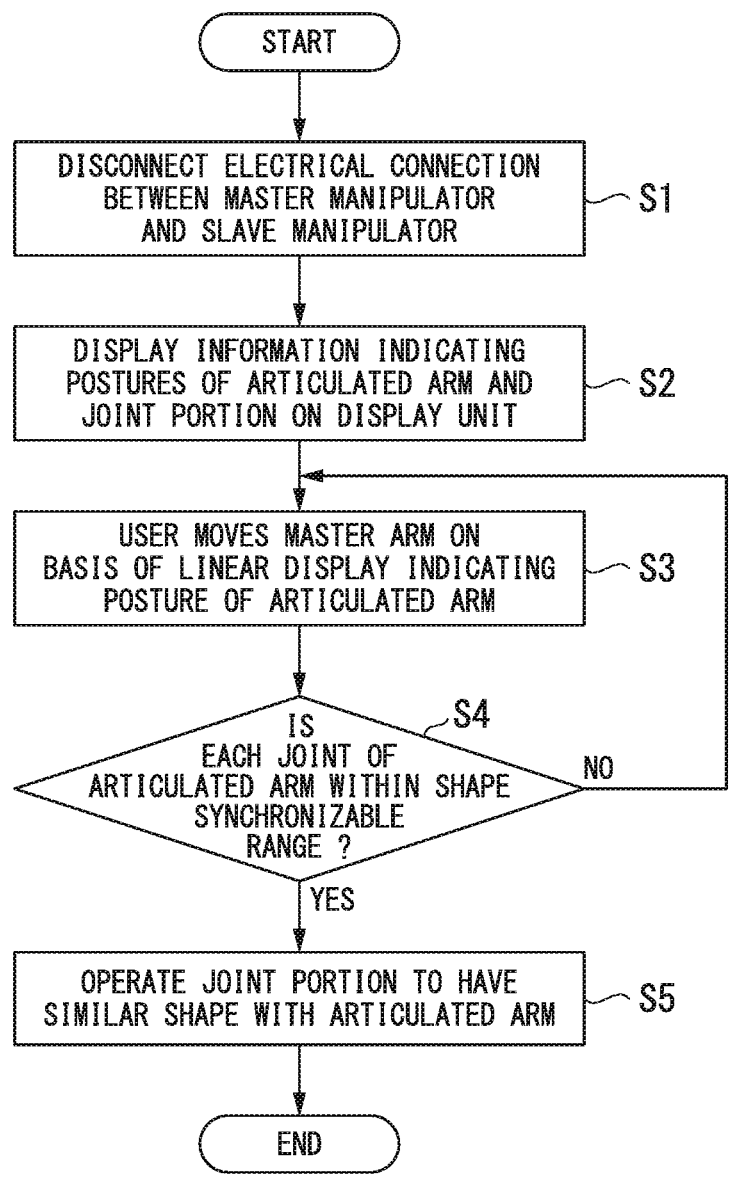
FIG. 5 is a flowchart showing an operation of the medical manipulator system.
Figure 6:
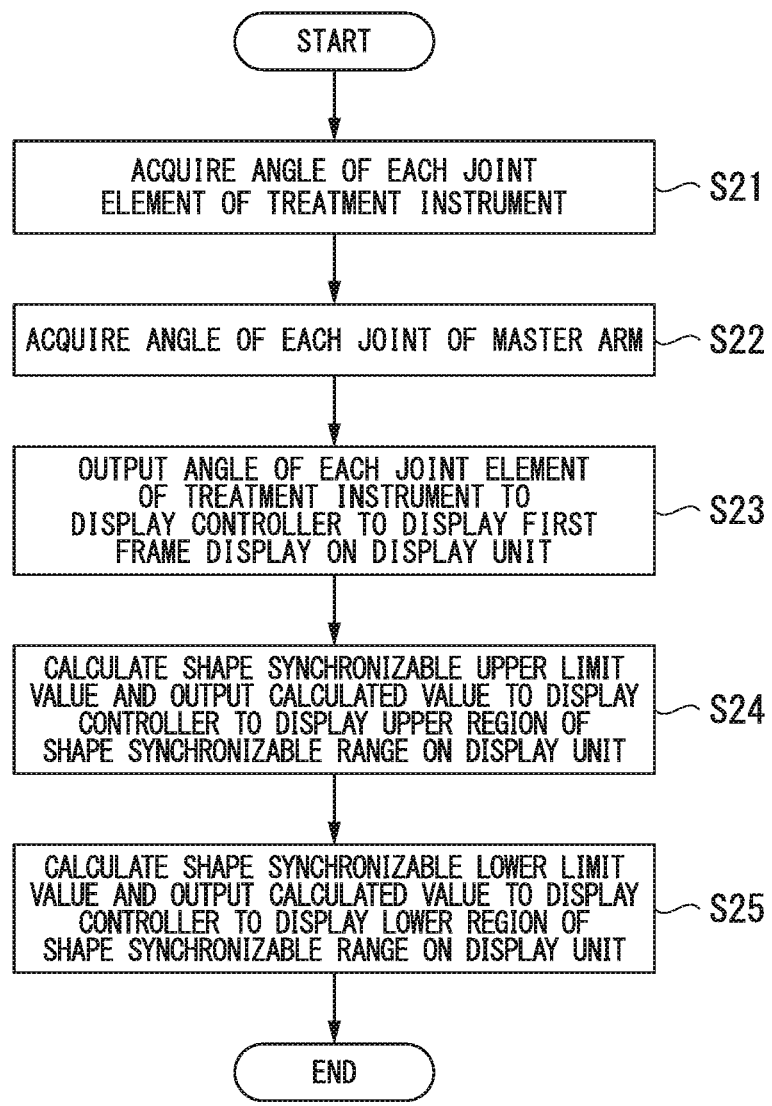
FIG. 6 is a flowchart showing an operation of the medical manipulator system.

An operation of the medical manipulator system 1 of the present embodiment will be described. FIG. 5 is a flowchart showing an operation of the medical manipulator system. FIG. 6 is a flowchart showing an operation of the medical manipulator system. FIG. 7 is a schematic view showing an example of a screen display of a display unit in the medical manipulator system.

In the medical manipulator system 1 of the present embodiment shown in FIG. 1, the treatment instrument 15 provided in the slave manipulator 10 operates when a user operates the operation input device 3 provided in the master manipulator 2.

Also, the joint portion 18 of the treatment instrument 15 is maintained to have a similarity relation with the articulated arm 4b of the operation input device 3. The position and orientation of the end effector 16 and the joint portion 18 inside the body are controlled by the controller 30 to be interlocked with a position and orientation of the operation unit 4 and the articulated arm 4b.

Meanwhile, while the treatment instrument 15 can be operated by the motor unit 24, there is no means to operate the operation input device 3 such as an actuator in the operation input device 3. Accordingly, in the third mode in which the treatment instrument 15 is configured not to operate according to the operation input device 3, the operator can freely change the orientation in the operation input device 3 while the position and orientation of the treatment instrument 15 just before shifting to the third mode are maintained. In this case, a situation in which the position or orientation of the articulated arm 4b of the operation input device 3 and the position or orientation of the joint portion 18 of the treatment instrument 15 do not have a similarity relation occurs.

When the above situation occurs, the controller 30 can execute the following flow to restore the similarity relation between the joint portion 18 of the treatment instrument 15 and the articulated arm 4b of the operation input device 3.

First, based on the input or the like on the master manipulator 2 by the user, the controller 30 shifts from the first mode (or the third mode) to the above-described second mode to restore the similarity relation between the joint portion 18 of the treatment instrument 15 and the articulated arm 4b of the operation input device 3.

In the second mode, first, the mode controller 33 disconnects an electrical connection between the master manipulator 2 and the slave manipulator 10 (step S1 shown in FIG. 5). In step S1, for example, the mode controller 33 disconnects a part of the electrical connection between the master manipulator 2 and the slave manipulator 10. Due to step S1, for example, a command from the master controller 31 to the slave controller 32 is invalidated by the mode controller 33 so that the treatment instrument 15 does not operate even while the operation input device 3 operates.

Thereby, step S1 ends and the flow proceeds to step S2.

Step S2 shown in FIG. 5 is a step in which information indicating orientations of the articulated arm 4b and the joint portion 18 are displayed on the display unit 8.

In step S2, the joint angle calculator 34 outputs the information indicating the angle of each joint 6 of the articulated arm 4b and the joint portion 18 of the treatment instrument 15, the information indicating the movable range of each joint element 19 provided in the joint portion 18 of the treatment instrument 15, and the information indicating the shape synchronizable range described above to the display controller 35. The display controller 35, for example, displays a figure corresponding to the above-described information on the display unit 8 as shown in FIG. 7. The user can ascertain a relative position of the articulated arm 4b with respect to the joint portion 18 of the treatment instrument 15 and the presence and size of a deviation of the orientations therebetween.

An example of a generation flow of the first frame display 41, the second frame display 42, and the linear display 43 in step S2 will be described in detail.

First, the joint angle calculator 34 acquires the joint angle of each joint element 19 from each encoder 26 provided in the joint portion 18 of the treatment instrument 15 (see S21 shown in FIG. 6).

After step S21, the joint angle calculator 34 acquires the joint angle of each joint 6 from each encoder 7 provided in the articulated arm 4b of the operation input device 3 (see S22 shown in FIG. 6).

After step S22, the joint angle calculator 34 outputs the joint angle acquired by the joint angle calculator 34 in the above-described step S21 to the display controller 35. The display controller 35 displays the first frame display 41 in a rectangular shape centered on the joint angle (the angle of each joint element 19 of the treatment instrument 15) acquired in step S21 and having upper and lower limits of the movable range of each joint element 19 at opposite ends on the display unit 8 (see step S23 shown in FIG. 6).

After step S23, the joint angle calculator 34 calculates a shape synchronizable upper limit value on an upper limit side of the movable range of each joint element 19 and outputs the calculated value to the display controller 35. The display controller 35 highlights a range from a center of the first frame display 41 to the shape synchronizable upper limit value in the first frame display 41 (see step S24 shown in FIG. 6). In step S24, the display controller 35 displays an upper region of the shape synchronizable range on the display unit 8. The highlight in step S24 refers to a displaying means for allowing the shape synchronizable range to be distinguishable in the first frame display 41 in such a manner that a boundary line at the shape synchronizable upper limit value or a range from the center of the first frame display 41 to the shape synchronizable upper limit value is indicated in a rectangular shape with a predetermined emphasis color.

After step S24, the joint angle calculator 34 calculates a shape synchronizable lower limit value on a lower limit side of the movable range of each joint element 19 and outputs the calculated value to the display controller 35. The display controller 35 highlights a range from the center of the first frame display 41 to the shape synchronizable lower limit value in the first frame display 41 (see step S25 shown in FIG. 6). In step S25, the display controller 35 displays a lower region of the shape synchronizable range on the display unit 8. The highlight in step S25 refers to a displaying means for allowing the shape synchronizable range to be distinguishable in the first frame display 41 in such a manner that a boundary line to the shape synchronizable lower limit value or a range from the center of the first frame display 41 to the shape synchronizable lower limit value is indicated in a rectangular shape with a predetermined emphasis color.

By displaying the second frame display 42, for example, in the first frame display 41 in which the movable range of each joint element 19 is indicated in step S24 and step S25 described above, the shape synchronizable range is partitioned.

After step S25, the display controller 35 starts an operation for displaying the linear display 43 on the display unit 8 so that the linear display 43 is overlapped in the first frame display 41 generated in above-described step S23 based on the joint angle (the angle of each joint 6 of the articulated arm 4b) acquired in step S22.

Step S25 is repeatedly executed until the second mode ends and the mode is shifted to the first mode. Thereby, the linear display 43 is updated at predetermined intervals to indicate a current angle of each joint 6 in the first frame display 41.

Following the flow from step S21 to step S25 described above, step S3 shown in FIG. 5 starts.

Step S3 is a step in which the user moves the operation input device 3 based on the linear display 43 indicating the orientation of the articulated arm 4b.

In step S3, the linear display 43 indicating the angle of the articulated arm 4b is updated according to the operation in which the user manually moves the operation input device 3. The linear display 43 displayed on the display unit 8 moves in the range of the first frame display 41 according to the operation of the operation input device 3 by the user. The user moves the operation input device 3 so that the linear display 43 is positioned inside the shape synchronizable range.

The movement of the operation input device 3 in step S3 is not a precise alignment of the articulated arm 4b with respect to the joint portion 18 of the treatment instrument 15 and the angle of each joint 6 of the articulated arm 4b may only be within the allowable range defined as the shape synchronizable range. Thus, it is easy for the user to manually perform the operation of moving the operation input device 3.

Thereby, step S3 ends and the flow proceeds to step S4.

Step S4 shown in FIG. 5 is a step in which it is determined whether or not all joints 6 of the articulated arm 4b are within the shape synchronizable range.

In step S4, step S4 is repeated until it is determined that each joint 6 of the articulated arm 4b is within the shape synchronizable range, and the flow proceeds to step S5 when it is determined that all joints 6 of the articulated arm 4b are within the shape synchronizable range.

Step S5 starts after the condition that all joints 6 of the articulated arm 4b be within the shape synchronizable range is satisfied in step S4. Step S5 is a step in which the joint portion 18 is operated to have a similar shape to that of the articulated arm 4b.

In step S5, the slave controller 32 operates the joint portion 18 such that the joint portion 18 of the treatment instrument 15 satisfies the similarity relation corresponding to the position and orientation of the articulated arm 4b of the operation input device 3. For example, in step S5, the joint angle calculator 34 operates the joint portion 18 of the treatment instrument 15 so that the angle of each joint 6 provided in the articulated arm 4b and the angle of each joint element 19 of the joint portion 18 of the treatment instrument 15 associated with the respective joints 6 coincide with each other. The articulated arm 4b and the joint portion 18 which have been roughly manually aligned within the shape synchronizable range in the above-described step S3 are precisely positioned with a similarity relation in step S5. The size of a movement region of the joint portion 18 in step S5 is narrow to such an extent that the end effector 16 and the joint portion 18 do not come into contact with tissues or the like inside the body because the articulated arm 4b are within the shape synchronizable range in step S3.

Thereby, step S5 ends, the mode shifts from the second mode to the first mode, and a treatment using the treatment instrument 15 can be started.

As described above, according to the medical manipulator system 1 of the present embodiment, the manual alignment by the user has only to be roughly within the shape synchronizable range. Therefore, compared to a case in which the operation input device 3 is manually operated until the position and orientation of the joint portion 18 of the treatment instrument 15 and the position and orientation of the articulated arm 4b of the operation input device 3 have an accurate similarity relation, it is possible to restore the similarity relation of the operation input device 3 and the treatment instrument 15 in a short period of time with a small movement amount.

The display controller 35 of the medical manipulator system 1 of the present embodiment associates the angle of each joint 6 of the articulated arm 4b with the angle of each joint element 19 of the joint portion 18 of the treatment instrument 15 and outputs it to the display unit 8. That is, the controller 30 of the present embodiment outputs the angle of each joint 6 of the articulated arm 4b with respect to the angle of each joint element 19 of the treatment instrument 15 to the display unit 8. As a result, it is easy for the user to recognize how much the operation input device 3 is deviated with respect to the treatment instrument 15, and it is possible to allow the user to intuitively understand how the operation input device 3 should be moved.

Modified Example 1

Figure 8:
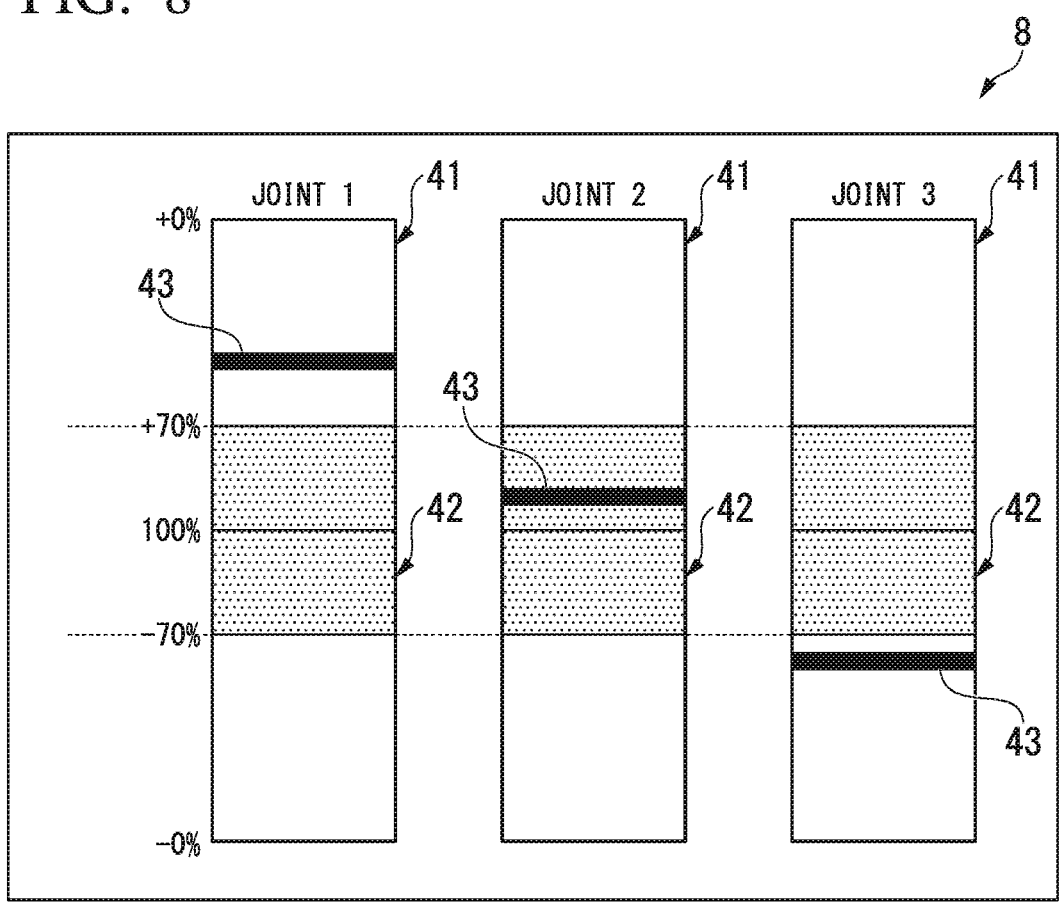
FIG. 8 is a schematic view showing an example of a screen display of a display unit in a modified example of the first embodiment.

A modified example of the above embodiment will be described. FIG. 8 is a schematic view showing an example of a screen display of a display unit in the present modified example.

In the present modified example, a display mode on the display unit 8 by the display controller 35 is different from that in the above-described embodiment.

In step S23 and step S24 in the above-described first embodiment, the display controller 35 in the present modified example outputs a difference of the angle of the corresponding joint 6 of the articulated arm 4b with respect to the current angle of the joint element 19 provided in the joint portion 18 of the treatment instrument 15 to the display unit 8 as a graph indicated in percentage as shown in FIG. 8.

For example, in the present modified example, the current angle of the joint element 19 of the treatment instrument 15 is set to 100% and set at the center of the first frame display 41, and limit points of the movable range of the joint element 19 are set to +0% and −0% and set at opposite ends of the first frame display 41. Here, +0% indicates that the angle of the corresponding joint 6 of the articulated arm 4b is at the limit point of the movable range of the joint element 19 in a positive direction (an upper limit side) of the movable range of the joint element 19. Also, −0% indicates that the angle of the corresponding joint 6 of the articulated arm 4b is at the limit point of the movable range of the joint element 19 in a negative direction (a lower limit side) of the movable range of the joint element 19.

In the present modified example, a larger absolute value of the percentage value indicated in the first frame display 41 represents that the angle of the corresponding joint 6 of the articulated arm 4b is closer to the current angle of the joint element 19 of the treatment instrument 15.

Even with such a display method, the same effect as the above-described embodiment is achieved.

In the present embodiment, since the movable range of each joint element 19 is indicated not by an angle but by a percentage, it can be displayed without discomfort using the first frame display 41 of the same size even when the angle of the absolute movable range of the joint element 19 is different for each element. As a result, in the present modified example, the screen display region of the display unit 8 can be used more efficiently than in the above-described embodiment.

Modified Example 2

Figure 9:
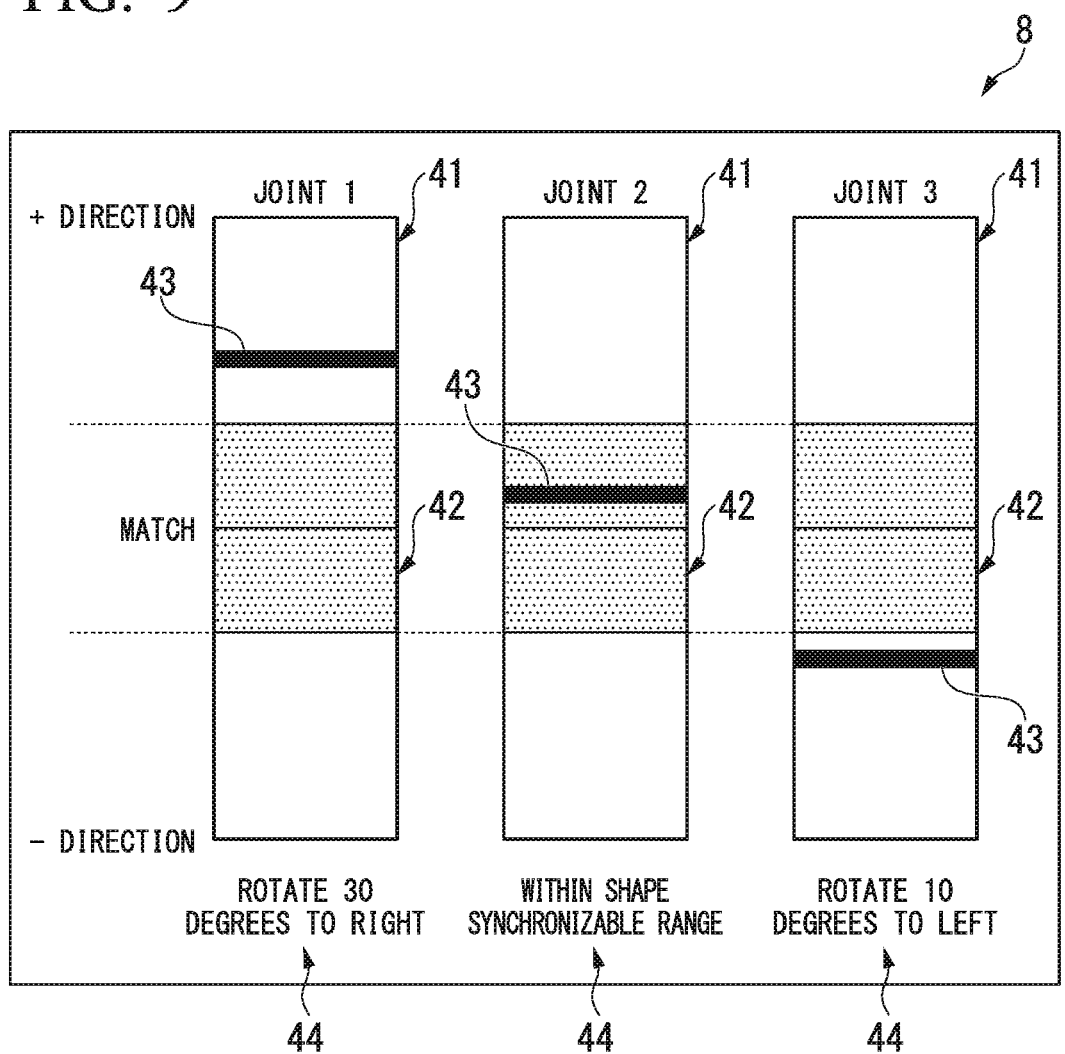
FIG. 9 is a schematic view showing an example of a screen display of a display unit in another modified example of the first embodiment.

Next, another modified example of the above-described embodiment will be described. FIG. 9 is a schematic view showing an example of a screen display of a display unit in the present modified example.

In the present modified example, how the articulated arm 4b should be operated to cause each joint 6 of the articulated arm 4b to be an angle within the shape synchronizable range is output from the display controller 35 to the display unit 8 and is displayed on the display unit 8.

For example, the joint angle calculator 34 acquires a direction of each joint 6 from the joint 6 closest to the proximal end of the articulated arm 4b to the operation unit 4 by forward kinematics calculation from the current individual angle information of each joint 6 of the articulated arm 4b provided in the operation input device 3.

Further, the display controller 35 generates a message 44 (see FIG. 9) indicating how the operation unit 4 should be moved using the direction of each joint 6 acquired by the joint angle calculator 34 and the angle and the shape synchronizable range of each joint element 19 of the joint portion 18 acquired by the joint angle calculator 34 in the same manner as in the above-described first embodiment. For example, the display controller 35 updates and displays the message 44 on the display unit 8 each time the linear display 43 indicating the angle of each joint element 19 is updated in step S25 in the above-described first embodiment.

In the present modified example, the user grasps the operation unit 4 and operates the articulated arm 4b, and thereby a bent state of the joint 6 configuring the articulated arm 4b changes. Since the user operates the operation unit 4 according to the message 44 which is output from the display controller 35 to the display unit 8 and is displayed on the display unit 8, the orientation of the articulated arm 4b of the operation input device 3 falls within the shape synchronizable range in which the similarity relation with the joint portion 18 of the treatment instrument 15 can be restored. The message 44 displayed on the display unit 8 indicates to the user how the articulated arm 4b should be moved to cause the angle of each joint 6 of the articulated arm 4b to coincide with the angle of each joint element 19 of the joint portion 18. Output of the message 44 to the display unit 8 by the display controller 35 includes calculating an operation procedure until the angle of each joint 6 of the articulated arm 4b coincides with the angle of each joint element 19 of the joint portion 18 and then outputting the operation procedure to the display unit 8.

In the present embodiment as described above, since the controller 30 calculates the operation procedure of the articulated arm 4b and outputs the operation procedure to the display unit 8, the user need only perform an operation according to the operation procedure and the similarity relation of the operation input device 3 and the treatment instrument 15 can be restored in a short period of time.

In the present modified example, the user may grasp the vicinity of each joint 6 configuring the articulated arm 4b to move the articulated arm 4b instead of grasping the operation unit 4. In this case, all the joints 6 can easily fall within the shape synchronizable range by sequentially moving each joint 6 according to the message 44 from the joint 6 positioned on a proximal end side of the articulated arm 4b toward the operation unit 4.

Second Embodiment

Figure 10:
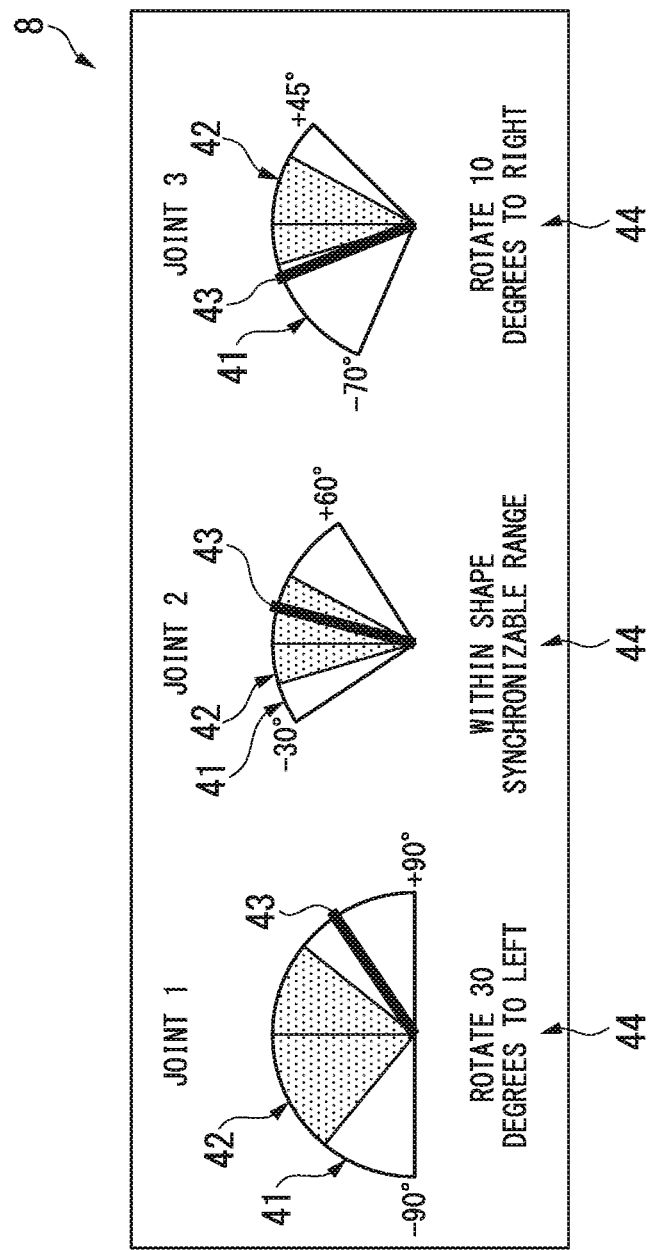
FIG. 10 is a schematic view showing an example of a screen display of a display unit in a medical manipulator system of a second embodiment of the present invention.

A second embodiment of the present invention will be described. Also, in each of the following embodiments, components common to the above-described first embodiment will be denoted by the same reference signs as in the first embodiment and duplicate description thereof will be omitted. FIG. 10 is a schematic view showing an example of a screen display of a display unit in a medical manipulator system of the present embodiment.

As shown in FIG. 10, in the present embodiment, a shape of a figure displayed on a display unit 8 is different from that of the above-described first embodiment. Specifically, in the present embodiment, a display controller 35 outputs a first frame display 41 and a second frame display 42 to the display unit 8 in a fan shape having a predetermined center. Further, the display controller 35 outputs a linear display 43 having an end at the above-described predetermined center and rotating about the predetermined center to the display unit 8 based on an angle of each joint 6 of an articulated arm 4b.

In the present embodiment, similarly to the second modified example of the first embodiment described above, the display controller 35 outputs a message 44 indicating how an operation input device 3 should be moved in a state in which an operation unit 4 is grasped on the display unit 8.

In the present embodiment, when a joint portion 18 and the articulated arm 4b have a plurality of rotating joints which rotate about predetermined axes, it is possible to convey to a user a degree of deviation of an orientation of the articulated arm 4b with respect to the joint portion 18 by intuitive display with a figure. As a result, it is intuitively understood by the user how each rotating joint should be moved to enable each joint 6 of the articulated arm 4b to be within a shape synchronizable range, and thus a similarity relation of the operation input device 3 and a treatment instrument 15 can be restored in a short period of time.

Third Embodiment

Figure 11:
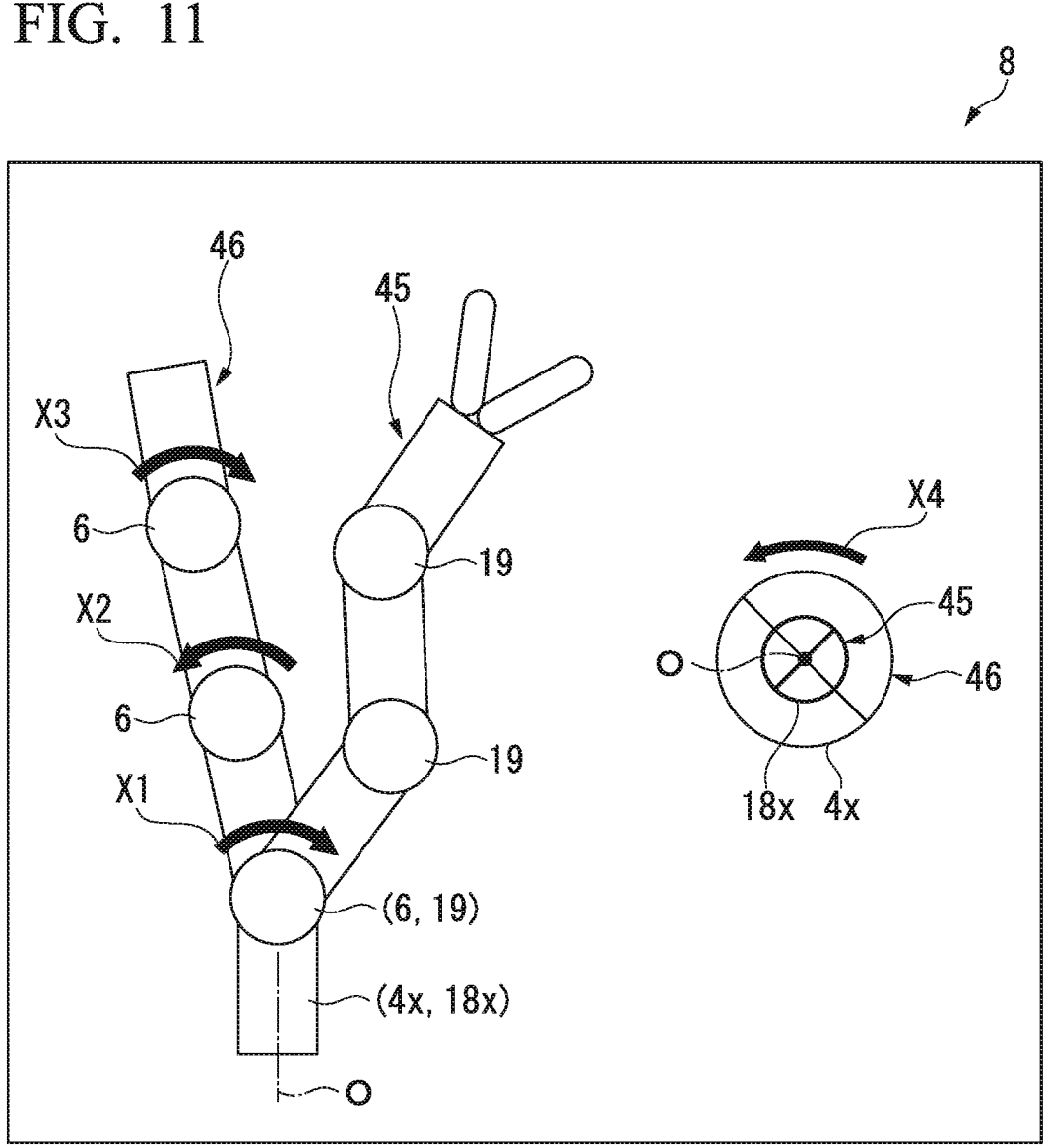
FIG. 11 is a schematic view showing an example of a screen display of a display unit in a medical manipulator system of a third embodiment of the present invention.

A third embodiment of the present invention will be described. FIG. 11 is a schematic view showing an example of a screen display of a display unit in a medical manipulator system of the present embodiment.

As shown in FIG. 11, in the present embodiment, a first computer graphics (CG) image 45 showing a shape of a joint portion 18 of a treatment instrument 15 and a second CG image 46 showing a shape of an articulated arm 4b are displayed in an overlapping manner on a display unit 8 by a display controller 35 (see FIG. 4).

The display controller 35 causes the first CG image 45 and the second CG image 46 to overlap in one image so that a joint element 19 closest to the proximal end side in a joint portion 18 of the treatment instrument 15 and a joint 6 closest to the proximal end side among joints 6 corresponding to the treatment instrument 15 in an articulated arm 4b overlap.

The first CG image 45 and the second CG image 46 are displayed on the display unit 8 in a second mode in which an operation input device 3 is moved to be similar to the joint portion 18 of the treatment instrument 15.

Similarly to the second modified example of the first embodiment described above, the display controller 35 displays a message 44 indicating how the articulated arm 4b should be moved so that the first CG image 45 and the second CG image 46 overlap more. In the present embodiment, the message 44 indicating how the articulated arm 4b should be moved is displayed in the vicinity of each joint 6 of the articulated arm 4b by symbols or the like for each joint 6. For example, the message 44 indicating how the articulated arm 4b should be moved may be an arcuate arrow (shown as reference signs X1, X2, and X3 in FIG. 11) about a rotation center of each joint 6 configuring the articulated arm 4b.

Two sets or more of the first CG image 45 and the second CG image 46 may be generated to show the joint portion 18 and the articulated arm 4b from a plurality of viewpoints.

For example, in addition to a first set of images (shown on the left side in FIG. 11) including such an image of the treatment instrument 15 in a plan view, the display controller 35 may display a second set of images (shown on the right side in FIG. 11) including such an image of the treatment instrument 15 seen from a proximal end side toward a distal end side on the display unit 8. In this case, as the message 44 indicating how the articulated arm 4b should be moved, a root portion 4x positioned on the proximal end side with respect to each joint 6 configuring the articulated arm 4b and an arrow in a circular arc shape (shown as a reference sign X4 in FIG. 11) about a center line O of the proximal end of the joint portion 18 may be in the second set of images.

In the present embodiment, since it is possible to use the CG image that allows easy understanding of the positional correlation between the treatment instrument 15 and the articulated arm 4b, the similarity relation of the operation input device 3 and the treatment instrument 15 can be restored in a shorter time by an intuitive operation performed by the user than by the operation based on the graphical display as in the first embodiment or the second embodiment.

While embodiments of the present invention have been described in detail above with reference to the accompanying drawings, the specific configurations are not limited to the embodiments but may include design changes without departing from the spirit of the present invention.

Moreover, the components represented in each of the embodiments and modifications thereto can be configured by an appropriate combination thereof.

In addition, a configuration can be adopted by appropriately combining the configuration elements described in the respective embodiments and the respective modification examples with each other. The present invention is not limited by the above description, and is limited by only appended claims.

What is claimed is:

1. A medical manipulator system comprising:
a slave manipulator having a first joint;
a first encoder detecting an orientation of the first joint;
a master manipulator having a second joint associated with the first joint for operating the first joint;
a second encoder detecting an orientation of the second joint;
a controller configured to output a signal for operating the first joint, the signal being based on the orientation of the second joint detected by the second encoder; and
a display displaying information output by the controller,
wherein a display of the information by the display includes a first display and a second display, the first display indicating a predetermined range centered on the orientation of the first joint that is detected by the first encoder, and the second display indicating the orientation of the second joint that is detected by the second encoder.

2. The medical manipulator system according to claim 1, wherein the controller outputs a signal for operating the first joint such that an angle of the first joint coincides with an angle of the second joint, when the orientation of the second joint is within the range indicated by the first display.

3. The medical manipulator system according to claim 1, wherein the controller outputs the information indicating an angle of the second joint with respect to an angle of the first joint to the display.

4. The medical manipulator system according to claim 3, wherein the controller calculates an operation procedure of the second joint until the angle of the second joint coincides with the angle of the first joint based on the angle of the first joint and the angle of the second joint and the controller outputs the information indicating the calculated operation procedure to the display.

* * * * *